US006004815A

United States Patent [19]

Portnoy et al.

[11] Patent Number: 6,004,815

[45] Date of Patent: Dec. 21, 1999

[54] BACTERIA EXPRESSING NONSECRETED CYTOLYSIN AS INTRACELLULAR MICROBIAL DELIVERY VEHICLES TO EUKARYOTIC CELLS

[75] Inventors: Daniel A. Portnoy; Darren E. Higgins, both of Berkeley, Calif.

[73] Assignee: The Regents of the University of California, Oakland, Calif.

[21] Appl. No.: 09/133,914

[22] Filed: Aug. 13, 1998

[51] Int. Cl.$^6$ .............................. C12N 1/21; C12N 5/10; A61K 39/00

[52] U.S. Cl. ................. 435/454; 435/252.3; 435/252.33; 435/325; 435/373; 424/200.1

[58] Field of Search ............................ 435/252.3, 252.33, 435/325, 373, 454; 424/200.1

[56] References Cited

U.S. PATENT DOCUMENTS

| | | | |
|---|---|---|---|
| 4,888,170 | 12/1989 | Curtiss, III | 424/200.1 |
| 5,294,441 | 3/1994 | Curtiss, III | 424/200.1 |
| 5,387,744 | 2/1995 | Curtis, III et al. | 424/258.1 |
| 5,424,065 | 6/1995 | Curtis, III et al. | 424/93.2 |
| 5,824,538 | 10/1998 | Branstrom et al. | 435/252.1 |
| 5,855,879 | 1/1999 | Curtis, III | 424/93.2 |
| 5,855,880 | 1/1999 | Curtiss, III et al. | 424/93.2 |
| 5,877,159 | 3/1999 | Powell et al. | 514/44 |

OTHER PUBLICATIONS

Darji et al., Cell 91:765–775 (1997).

Higgins et al., Molecular Microbiology 31(6):1631–1641 (1999).

Higgins et al., Nature Biotechnology 16(2):138–139 (1998).

Ikonomidis et al., Journal of Experimental Medicine 180(6):2209–2218 (1994).

*Primary Examiner*—Johnny F. Railey, II

*Attorney, Agent, or Firm*—Richard Aron Osman

[57] ABSTRACT

The invention provides methods and compositions relating to intracellular delivering of agents to eukaryotic cells. The compositions include microbial delivery vehicles such as nonvirulent bacteria comprising a first gene encoding a nonsecreted foreign cytolysin operably linked to a heterologous promoter and a second gene encoding a different foreign agent. The foreign agent may be a nucleic acid or protein, and is frequently bioactive in and therapeutic to the target eukaryote. In addition, the invention provides eukaryotic cells comprising the subject nonvirulent bacteria and nonhuman eukaryotic host organisms comprising such cells.

33 Claims, 2 Drawing Sheets

SEQUENCE LISTING

<160> NUMBER OF SEQ ID NOS: 6

<210> SEQ ID NO 1
<211> LENGTH: 34
<212> TYPE: DNA
<213> ORGANISM: Listeria monocytogenes

<400> SEQUENCE: 1
ggaattccat atgaaggatg catctgcatt caat 34

-continued

```
<210> SEQ ID NO 2
<211> LENGTH: 33
<212> TYPE: DNA
<213> ORGANISM: Listeria monocytogenes

<400> SEQUENCE: 2

cgggatcctt attattcgat tggattatct act                              33


<210> SEQ ID NO 3
<211> LENGTH: 26
<212> TYPE: DNA
<213> ORGANISM: Listeria monocytogenes

<400> SEQUENCE: 3

cgcgatatcc tctagaaata attttg                                      26


<210> SEQ ID NO 4
<211> LENGTH: 32
<212> TYPE: DNA
<213> ORGANISM: Listeria monocytogenes

<400> SEQUENCE: 4

aggcgtcgac ggttaatacg accgggatcg ag                               32


<210> SEQ ID NO 5
<211> LENGTH: 40
<212> TYPE: DNA
<213> ORGANISM: Listeria monocytogenes

<400> SEQUENCE: 5

aggcgtcgac aggccttacg cgaaatacgg gcagacatgg                       40


<210> SEQ ID NO 6
<211> LENGTH: 8
<212> TYPE: PRT
<213> ORGANISM: murine

<400> SEQUENCE: 6

Ser Ile Ile Asn Phe Glu Lys Leu
  1               5
```

BACTERIA EXPRESSING NONSECRETED CYTOLYSIN AS INTRACELLULAR MICROBIAL DELIVERY VEHICLES TO EUKARYOTIC CELLS

The disclosed inventions were made with Government support under Grant (Contract) Nos. A127655-10 BD37 awarded by the National Institutes of Health. The government may have rights in these inventions.

INTRODUCTION

1. Field of the Invention

The field of this invention is microbial-based intracellular delivery of agents to eukaryotic cells.

2. Background

The efficient delivery of macromolecules to the cytosol of mammalian cells is of fundamental importance in such processes as the generation of transfected phenotypes and ithe study of protein function and localization. Furthermore, delivery of macromolecules to the cytosol is also important for the induction of cell-mediated immunity and is a significant challenge facing the rational design of vaccines to intracellular pathogens. Numerous methodologies currently exist for delivering macromolecules to mammalian cells. These include but are not limited to: mechanical techniques such as electroporation (1) and microinjection (2); fusion methodologies such as fusion with vesicles and liposomes (2); chemical treatments employing the use of ATP or EDTA (3) or the external addition of molecules mixed with pore-forming toxins such as α-toxin of *Staphylococcus aureus* (4). Many of these methods have a disadvantage in that the molecule to be delivered may require laborious purification (i.e. protein) or the delivery method is limited to use in vitro. In order to overcome these obstacles, investigators have sought to use biological vectors that can enter tissues, cells and specific cellular compartments for the delivery of macromolecules. These vectors are often derived from either retroviruses or bacteria that have evolved to invade and replicate in specific hosts, organs, or cell types. While retroviral vectors have been used for the delivery and subsequent expression of DNA in host cells (5–7), bacterial vectors have been exploited primarily for the delivery of antigenic proteins and more recently adapted for the delivery of DNA to mammalian cells (8–12).

Relevant Literature

Lee et al. (1997) U.S. Pat. No. 5,643,599 and Lee et al. (1996) *J.Biol. Chem.* 271, 7249–7252 describe hemolysin loaded liposomes for intracellular delivery of macromolecules. Dietrich, G., et al. (1998) *Nature Biotech.* 16, 138–139 and Ikonomidis, G., et al. (1997) *Vaccine* 15, 433–440 describe the use of *Listeria monocytogenes* as a macrophage delivery vehicle. Sizemore, D. R., Branstrom, A. A., & Sadoff, J. C. (1995) *Science* 270, 299–302 and Courvalin, P., et al. (1995) *C. R Acad. Sci. III* 318, 1207–1212 describe the use of attenuated Shigella and invasive strains of *Shigella flexneri* and *E. coli*, respectively, as a DNA delivery vehicle. Hess, J., et al. (1998) *Proc. Natl. Acad. Sci. U. S. A.* 95, 5299–5304; and Darji, A., et al. (1995) *J. Biotechnol* 43, 205–212 describe the expression of listeriolysin in several heterologous systems: an invasive *E. coli, Mycobacterium bovis* and *Listeria innocua*, respectively. Moriishi et al. (1996) *FEWS Immunol. Med. Microbiol.* 16, 213–222, 217 describe the transformation of an *E. coli* with a plasmid encoding listeriolysin. Sanderson, S., Campbell, D. J., & Shastri, N. (1995) *J. Exp. Med.* 182, 1751–1757, describe the cloning of a *Listeria monocytogenes* genomic library in *E. coli*. Higgins and Portnoy (1998) *Nature Biotech.* 16, 181–185 review bacterial delivery of DNA.

SUMMARY OF THE INVENTION

The invention provides methods and compositions relating to intracellular delivering of agents to eukaryotic cells. The compositions include microbial delivery vehicles such as nonvirulent bacteria comprising a first gene encoding a nonsecreted foreign cytolysin operably linked to a heterologous promoter and a second gene encoding a different foreign agent. In particular embodiments, the bacteria may be variously invasive to the target cell, autolysing within target cell endosomes and preferably, a laboratory strain of *E. coli*. The cytolysin may lack a functional signal sequence, and is preferably a listeriolysin. The foreign agent may be a nucleic acid or protein, and is frequently bioactive in and therapeutic to the target eukaryote. In addition, the invention provides eukaryotic cells comprising the subject nonvirulent bacteria and nonhuman eukaryotic host organisms comprising such cells. The invention also provides methods for introducing foreign agents into eukaryotic cells comprising the step of contacting the cell in vivo or in vitro with the subject bacteria under conditions whereby the agent enters the cell. In particular embodiments, the bacterium is endocytosed into a vacuole of the cell, undergoes lysis and the cytolysin mediates transfer of the agent from the vacuole to the cytosol of the cell.

DETAILED DESCRIPTION OF PREFERRED EMBODIMENTS OF THE INVENTION

Figure 1:
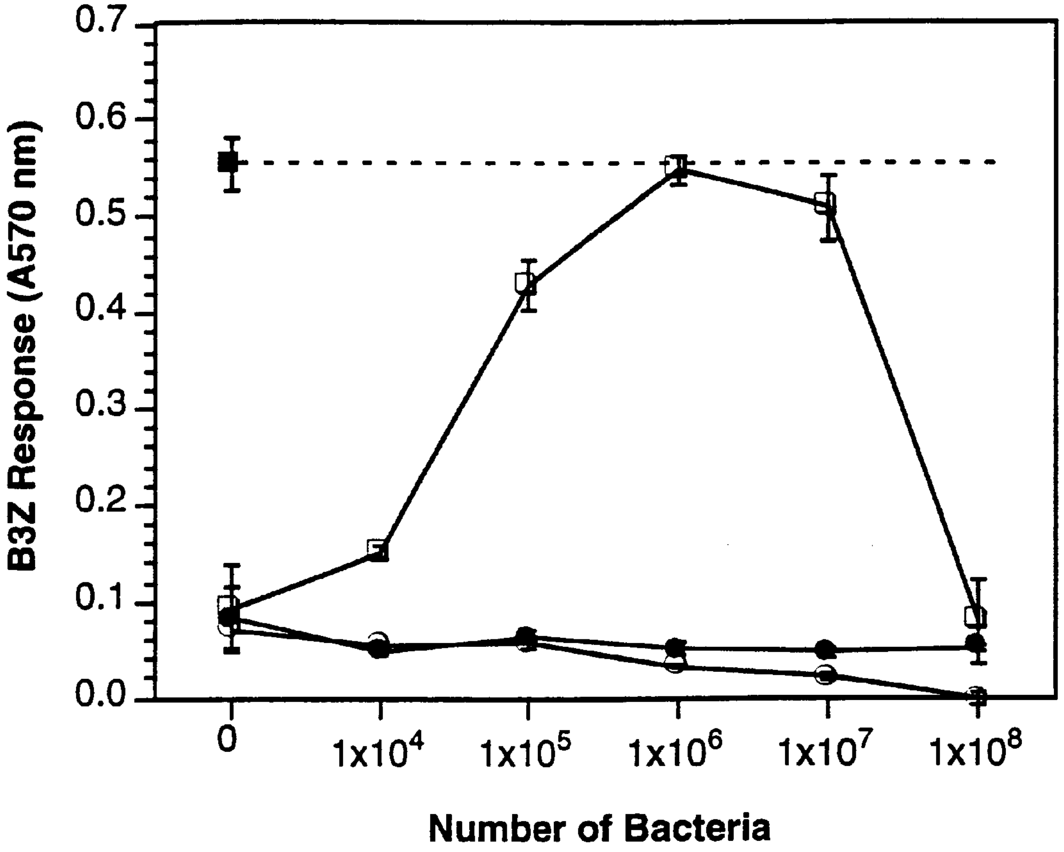
FIG. 1. Presentation of SL8/$K^b$ complex to B3Z T-cells.

The following preferred embodiments and examples are offered by way of illustration and not by way of limitation.

The subject bacteria comprise a first gene encoding a nonsecreted foreign cytolysin operably linked to a heterologous promoter. A wide variety of foreign (i.e. not native to the microbial delivery vehicle) cytolysins may be used so long as the cytolysin is not significantly secreted by the microbe and facilitates cytosolic delivery of the foreign agent as determined by the assays described below. Exemplary cytolysins include phospholipases (see, e.g., Camilli, A., et al., *J. Exp. Med.* 173:751–754 (1991)), pore-forming toxins (e.g., an alpha-toxin), natural cytolysins of gram-positive bacteria, such as listeriolysin O (LLO, e.g. Mengaud, J., et al., *Infect. Immun.* 56:766–772 (1988) and Portnoy, et al., Infect. Immun. 60:2710–2717 (1992)), streptolysin O (SLO, e.g. Palmer M, et al., 1998, Biochemistry 37(8):2378–2383) and perfringolysin O (PFO, e.g. Rossjohn J, et al., Cell 89(5):685–692). Where the target cell is phagosomal, acid activated cytolysins may be advantageously used. For example, listeriolysin O exhibits greater pore-forming ability at mildly acidic pH (the pH conditions within the phagosome), thereby facilitating delivery of the liposome contents to the cytoplasm (see, e.g., Portnoy, et al., *Infect. Immun.* 60:2710–2717 (1992)). Furthermore, natural cytolysins are readily modified to generate mutants which are screened in the assays described below or otherwise known in the art (e.g. Awad MM, et al., Microb Pathog. 1997, 22(5): 275–284) desired activity modifications. In general, the screening assays measure the ability of a candidate cytolysin to confer on a bacterium the ability to render a target cell vacuole permeable to a label (e.g., a fluorescent or radioactive label) that is contained in the vacuole. In a particular example, the invention provides mutations in natural cytolysin wherein highly conserved cysteine residues (e.g., cysteine 460 in PFO, cysteine 486 in LLO) are replaced by conservative amino acid substitutions which are not subject to reduction in order to prepare oxidation/reduction-insensitive cytolysin mutants which exhibit improved lytic activity. Alternatively, mutant cytolysins are selected from naturally occurring mutants by, for example, identifying bacteria which contain cytolysins that are capable of lysing cells over a narrow pH range, preferably the pH range which occurs in phagosomes (pH 5.0–6.0), or under other conditions (e.g., ionic strength) which occur in the targeted phagosomes. Nonsecreted cytolysins may be provided by various mechanisms, e.g. absence of a functional signal sequence, a secretion incompetent microbe, such as microbes having genetic lesions (e.g. a functional signal sequence mutation), or poisoned microbes, etc.

The bacteria also comprise a second gene encoding a foreign agent different from the cytolysin, and the subject methods may be used to deliver a wide variety of such foreign agents for a variety of applications, including diagnosis, therapy including prophylactics such as immunizations (see, e.g. HIV vaccine, Table 1) and treatments such as gene therapy (especially of single gene disorders amenable to localized treatment, see Table 1, below), biosynthesis, etc.; essentially any agent that the microbial host can be engineered to produce. In a particular embodiment, the agent is largely retained by the microbe until lysis within the target cell vacuole. Note that the first and second genes may be the same, i.e. the same nucleic acid encodes both the cytolysin and the foreign agent. For example, in a particular embodiment, the foreign agent is expressed in frame with the cytolysin as a fusion protein. In other embodiments, the microbes are engineered to deliver libraries of agents for screening, e.g. Tenson T, et al., *J Biol Chem* Jul. 11, 1997;272(28):17425–17430.

A wide variety of nucleic acid-based agents may be delivered, including expression vectors, probes, primers, antisense nucleic acids, knockout/in vectors, ribozymes, etc. For example, the subject bacteria are used to deliver nucleic acids which provide templates for transcription or translation or provide modulators of transcription and/or translation by hybridizing to selected endogenous templates, see, e.g. U.S. Pat. No. 5,399,346 for a non-limiting list of genes that can be administered using gene therapy and diseases that can be treated by gene therapy. For example, polynucleotide agents may provide a coding region operably linked to a transcriptional regulatory region functional in a target mammalian cell, e.g. a human cytomegalovirus (CMV) promoter. In particular, the polynucleotide may encode a transcription factor, whereby expression of the transcription factor in the target cell provides activation or de-activation of targeted gene expression in the target cell. In another example, RNA virus infected cells are targeted by microbes delivering viral RNA-specific ribozymes, e.g. HIV-infected T-cells, leukemia virus infected leukocytes, hepatitis C infected liver cells. In yet another embodiment, labeled probes are delivered which effect in situ hybridization-based diagnostics.

A wide variety of polypeptide-based agents may also be delivered, including antibiotics, insecticides, fungicides, anti-viral agents, anti-protozoan agents, enzymes, anti-cancer agents (e.g. cyclin dependent kinase (CDK) inhibitors such as P16, P21 or P27), antibodies, anti-inflammatory peptides, transcription factors, antigenic peptides, etc. Exemplary therapeutically active polypeptides which can be delivered by the subject invention are described in Nature Biotech 16(2), entire issue, etc. In a particular embodiment, the invention provides for the delivery to antigen-presenting cells of antigenic polypeptides which are presented in association with MHIC proteins. In another particular embodiment, both nucleic acids and proteins are delivered together contemporaneously, in the same administration or in the same microbe. In some such applications, the nucleic acids and proteins can act in concert, e.g. an integrating vector and an integrase, and RNA and a reverse transcriptase, a transposon and a transposase, etc.

The subject methods may also be used to deliver a wide variety of other foreign agents that are synthesized by the host microbe. For example, microbes may be selected for, or engineered to contain, biosynthetic machinery to produce any microbiologically producible agent compatible with the subject methods (e.g. sufficiently microbe impermeant to provide effective delivery to the target cell). Preferred such agents are those that are contraindicated for convenient direct (e.g. oral) administration, because of, for example, gut inactivation, toxicity, intolerance, impermeability, etc. In fact, even agents providing significant toxicity to the microbial host find use so long as an effective amount of the agent may be loaded (by synthesis) or maintained in the microbe (see, e.g. LLO toxicity, below).

A wide variety of nonvirulent, non-pathogenic bacteria may be used; preferred microbes are relatively well characterized strains, particularly laboratory strains of *E. coli*, such as MC4100, MC1061, DH5α, etc. Other bacteria that can be engineered for the invention include well-characterized, nonvirulent, non-pathogenic strains of *Listeria monocytogenes, Shigella flexneri*, mycobacterium, Salmonella, *Bacillus subtilis*, etc. In a particular embodiment, the bacteria are attenuated to be nonreplicative, nonintegrative into the host cell genome, and/or non-motile inter- or intra-cellularly. A wide variety of suitable means for microbial attenuation are known in the art. In another particular embodiment, the bacteria are dead or non-viable prior to endocytosis by the target cell or administration to the target organism, obviating any microbial growth or metabolism in the target cell. A wide variety of suitable means for killing or rendering the bacteria nonviable are known in the art, including fixation with organic solvents such as methanol, UV irradiation, heat, freeze-drying, etc. Preferred methods preserve the ability of the microbial membrane and/or wall to retain the cytolysin and the foreign agent. In this embodiment, the first and second genes are sufficiently expressed to load the microbe with an effective amount of the cytolysin and foreign agent prior to microbial cell death. Generally the bacteria contain (i.e. are loaded by expression within the bacteria with) with from about ten to one thousand, preferably from about one hundred to one thousand cytolysin molecules per bacterium.

The microbes of the invention can be used to deliver the foreign agent to virtually any target cell capable of endocytosis of the subject microbe, including phagocytic, non-phagocytic, pathogenic or diseased cells. Exemplary target animal cells include epithelial cells, endothelial cells, muscle cells, liver cells, pancreatic cells, neural cells, fibroblasts, tumor cells, leukocytes such as macrophages, neutrophils, B-cells, T-cells, monocytes, etc., etc. The subject methods generally require microbial uptake by the target cell and subsequent lysis within the target cell vacuole (including phagosomes and endosomes). While phagocytic target cells generally provide for microbial uptake and lysis, for many cell types, it is necessary to provide the bacteria with an invasin to facilitate or mediate uptake by the target cell and an autolysin to facilitate or mediate autolysis of the bacteria within the target cell vacuole. A wide variety of suitable invasins and autolysins are known in the art. For example, both Sizemore et al. (*Science*, 1995, 270:299–302) and Courvalin et al. (*C.R. Acad. Sci. Paris*, 1995, 318:1207–12) teach expression of an invasin to effect endocytosis of the bacterium by a target cell and suitable microbial autolysins are described by Cao et al., *Infect Immun* 1998, 66(6): 2984–2986; Margot et al., *J. Bacteriol* 1998, 180(3):749–752; Buist et al., *Appl Environ Microbiol*, 1997, 63(7):2722–2728; Yamanaka et al., *FEMS Microbiol Lett*, 1997, 150(2): 269–275; Romero et al., *FEMS Microbiol Lett*, 1993, 108(1):87–92; Betzner and Keck, *Mol Gen Genet*, 1989, 219(3): 489–491; Lubitz et al., *J. Bacteriol*, 1984, 159(1):385–387; and Tomasz et al., *J. Bacteriol*, 1988, 170(12): 5931– 5934. Providing the advantage of delayed lysis are temperature-sensitive autolysins, time-sensitive autolysins (see, e.g. Chang et al., 1995*, J Bact* 177, 3283–3294; Raab et al., 1985, *J Mol Biol* 19, 95–105; Gerds et al., 1995*, Mol Microbiol* 17, 205–210) and addiction (poison/antidote) autolysins, (see e.g. Magnuson R, et al., 1996*, J Biol Chem.* 271(31), 18705–18710; Smith AS, et al., 1997*, Mol Microbiol.* 26(5), 961–970).

Administration of the microbe to target cells may be in vitro or in vivo according to conventional methodologies. In either case, the methods generally involve growing the microbes, inducing the expression of the first and second genes, and contacting the target cells with an effective amount of bacteria sufficient to effect the desired activity of the foreign agent in the target cell. Immunofluorescense may be used to image and track the contents of the bacteria upon administration to the cells in vivo or in vitro.

In vitro or ex vivo administration generally involves contacting the target cell with an effective amount of the microbes of the invention. Exemplary in vitro administrations are described and/or cited by reference below. In vitro applications include protein delivery (e.g. for functional determinations, toxin delivery to targeted cells in culture, half-life, degradation and localization determinations), nucleic acid delivery (e.g. DNA to transfected cell lines, genomic libraries to screen and identify specific antigens, i.e. expression cloning, etc.)

In vivo administration generally involves administering a pharmaceutical composition containing a therapeutically effective amount of the microbes of the invention. Generally, the therapeutically effective amount is between about 1 $\mu$g and 100 mg/kg, preferably between about 1 $\mu$g and 1 mg/kg. The microbes are formulated into a pharmaceutical composition by combination with an appropriate pharmaceutically acceptable excipient in accordance with routine procedures known to one of ordinary skill in the art. The microbes may be used alone or in appropriate association, as well as in combination with other pharmaceutically active compounds. The microbes may be formulated into preparations in solid, semisolid, or liquid form such as tablets, capsules, powders, granules, ointments, solutions, suppositories, and injections, in usual ways for topical, nasal, oral, parenteral, or surgical administration. Administration in vivo can be oral, mucosal, nasal, bronchial, parenteral, subcutaneous, intravenous, intra-arterial, intramuscular, intra-organ, intra-tumoral, surgical or in general by any means typical of a gene therapy administration. Administration will be selected as is appropriate for the targeted host cells. Target cells may also be removed from the subject, treated ex vivo, and the cells then replaced into the subject. Exemplary methods for in vivo administration are described in Shen et al., Proc Natl Acad Sci USA 1995, 92(9):3987–3991; Jensen et al, Immunol Rev 1997, 158: 147–157; Szalay et al., Proc Natl Acad Sci USA 1995, 92(26): 12389–12392; Belyi et al, FEMS Immunol Med Microbiol 1996, 13(3): 211–213; Frankel et al., J. Immunol 1995, 155(10):4775–4782; Goossens et al., Int Immunol 1995, 7(5):797–805; Schafer et al., J. Immunol 1992, 149(1):53–59; and Linde et al., Vaccine 1991, 9(2) :101–105.

The foregoing methods and compositions are demonstrated to be effective in a wide variety of exemplary applications. In one application, a K12 strain of *E. coli* is engineered with a signal sequence deficient LLO gene operably linked to the constitutive tet promoter for expressing the cytolysin in the bacterium and a second gene encoding a truncated BRCA1 cancer antigen, under regulatory control of a trc or tac promoter. The cytolysin and cancer antigen are expressed to maximum levels, the bacteria are then fixed with methanol, and the killed bacteria loaded with the cytolysin and cancer antigen are then injected into solid breast tumors in three weekly injections. At four weeks, a cancer antigen-specific cytotoxic T-cell response (CTL response) and tumor size reduction is detected. As shown in Table 1, analogous studies conducted in a variety of animals and animal cell types, both in vivo and in vitro, using a variety of agents, secretory deficient cytolysins, bacterial types and methods demonstrate consistent delivery of the agent to the target cell cytosol, as measured by agent activity, immunoassay, or other delivery monitoring assays described herein.

TABLE 1

Microbial-Based Delivery

| Target Cell | Indication | Agent | Lysin | Bacteria | Administration | Cytosol Delivery |
|---|---|---|---|---|---|---|
| transformed human macrophage | acites tumor in nude mice | human tumor antigen hTA1 | LLO | *E. coli*, JM109 (DE3) | intraperitoneal injection | +++ |
| rat liver | hepatocellular carcinoma | p51 tumor suppressor | $LLO^{M1}$ | *E. coli*, DP-E3619, invasin/autolysin | in situ; intratumor injection | +++ |
| rat kidney | genetic nephopathy | angiotensin converting enzyme | $LLO^{M2}$ | *S. typhimurium*, attenuated, invasin/autolysin | ex vivo | +++ |
| mouse brain | neuro-degeneration | cFos gene expression construct | $LLO^{M3}$ | *S. typhimurium*, attenuated, invasin/autolysin | in situ; intracranial implant | +++ |
| mouse pancreas | transformation | $\gamma$-interferon expression construct | $LLO^{M4}$ | *E. coli*, JM109 (DE3) | in vitro | +++ |
| pig muscle | muscular atrophy | insulin-like growth factor I (IGF-I) | PLO | *E. coli*, DP-E3618, invasin/autolysin | in situ; i.m. injection | +++ |
| human breast | transformation | anti-estrogen receptor antibody expression construct | SLO | *E. coli*, DP-E3617, invasin/autolysin | in vitro | +++ |

TABLE 1-continued

Microbial-Based Delivery

| Target Cell | Indication | Agent | Lysin | Bacteria | Administration | Cytosol Delivery |
|---|---|---|---|---|---|---|
| human prostate | localized prostatic carcinoma | ribozyme or antisense against CDK 2 or CDK4 | LLO | S. typhimurium, attenuated invasin/autolysin | in situ; intratumor injection | +++ |
| human lymphoid | lymphoma | tumor necrosis factor (TNF) | LLO | E. coli, DP-E3616 | ex vivo | +++ |
| human bone marrow | mylomoid leukemia | Hepatocyte growth factor/scatter factor (HGF/SF) | SLO | E. coli, DP-E3615 | ex vivo | +++ |
| human lymphoid | HIV infection | HIV RT gene-specific ribozyme | LLO | S. typhimurium, attenuated | ex vivo | +++ |
| human hepatic cells | Hepatitis C infection | Hepatitis C virus-specific ribozyme | LLO | S. typhimurium, attenuated, invasin/autolysin | in vivo; direct injection | +++ |
| human hepatic cells | diabetes | insulin receptor expression construct | LLO | S. typhimurium, attenuated, invasin/autolysin | in vivo; direct injection | +++ |
| human beta islet cells | diabetes | insulin expression construct | LLO | S. typhimurium, attenuated, invasin/autolysin | in vivo; direct injection | +++ |
| murine fibroblast | fibroblastoma | diptheria toxin | LLO | S. typhimurium, attenuated, invasin/autolysin | in vivo; direct injection | +++ |
| feline retinal cells | retinal degenerative disease | cGMP phosphodiesterase-beta | LLO | E. coli, JM109 (DE3), invasin/autolysin | intraocular injection | +++ |
| human cytotoxic T-cells | melanoma | melanosomal proteins | LLO | E. coli, JM109 (DE3) | in vivo; IV injection | +++ |
| human epithelium | Herpes infection | antisense RN AseP construct | LLO | S. typhimurium, attenuated, invasin/autolysin | in vivo; oral, opical abrasion | +++ |
| murine macrophages | IL-2 production | NFAT | LLO | S. typhimurium | in vitro | +++ |

$LLO^{M1-M4}$ are LLO mutants M1(Cys486Ser), M2(Cy486Met), M3(Trp492Ala) and M4(del491–493), respectively.

EXAMPLES

I. Delivery of Protein to the Cytosol of Macrophages Using *Escherichia coli* K-12 Expressing Listeriolysin O

*Listeria monocytogenes* is a bacterial pathogen that replicates within the cytosol of mammalian cells. *L. monocytogenes* has been used extensively as a model for the study of cell-mediated immunity and as a model pathogen for understanding the basis of intracellular pathogenesis (13, 14). Following internalization into host cells, bacteria are initially contained within host vacuoles then subsequently lyse these vacuoles to gain access to the cytosol. The ability of *L. monocytogenes* to lyse the vacuole and enter the cytosol is primarily mediated by listeriolysin O (LLO). LLO is a member of a family of related pore-forming cytolysins secreted by diverse species of gram positive bacteria (15). LLO encapsulated into pH-sensitive liposomes has been used as a vehicle to deliver co-encapsulated protein to the cytosol of macrophages (16). Moreover, purified LLO when mixed with foreign proteins and added to mammalian cells can mediate the delivery of protein to the cytosol and has been exploited for delivery to host cells both in vitro and in vivo (17–19). However, both of these methods require the purification of LLO and the protein to be delivered. Here, we show that *Escherichia coli* expressing cytoplasmic LLO can be used to efficiently deliver co-expressed proteins to the cytosol of macrophages. The utility of this system to deliver a large active protein to the cytosol was demonstrated by the delivery of *E. coli* β-galactosidase (β-gal). Using chicken ovalbumin (OVA) we demonstrate the rapid delivery of protein to the cytosol of macrophages and the ability of the *E. coli*/LLO system to efficiently deliver OVA to the MHC class I pathway of antigen processing and presentation. Moreover, the time required for processing and presentation of an OVA-derived peptide to $CD8^+$ T cells, when OVA was delivered using this system, was equivalent to that previously reported when purified OVA was introduced into the cytosol by alternative methods such as scrape-loading or liposomes (16, 20, 21).

Bacterial Strains and Plasmids. All bacterial strains and plasmids used in this report are listed in Table 2.

TABLE 2

*E. coli* strains and plasmids used in this work

| Strain or Plasmid | Description | Reference or source |
|---|---|---|
| pACYC184 | cloning vector; $Tc^r$ $Cm^r$ | (23) |
| pET28a | over-expression vector;$Kan^r$ | (Novagen, Inc.) |
| pBT29b | over-expression vector;$Kan^r$ | (Novagen, Inc.) |
| pTL61T | lacZ transcriptional fusion vector; $Ap^r$ | (24) |
| pBluescript SK- | cloning vector; $Ap^r$ | (Stratagene, Inc.) |
| pTrcHisC/Ova | pTrcHisC::ova | (D. Campbell, UCB) |
| pDP3615 | pACYC184 tet::hly | Herein |
| pDP3616 | pET28a pT7::ova | Herein |
| pDH70 | pBluescript SK-pT7::lacZ | Herein |
| MC4100(DE3) | $F^-$ araD139 Δ(argF-lac)U169 rpsL150 $(Str^r)$relA1 flbB5301 deoC1 ptsF25 rbsR with DE3, a λ prophage carrying the T7 RNA polymerase gene | (Schifferli, U.Penn) |
| JM109(DE3) | endA1 recA1 gyrA96 thi hsdR17 relA1 supE44 Δ(lac-proAB) [F' traD36 proAB $lacI^qZ$ΔM15] DE3 | (Promega, Co.) |
| DP-B3615 | MC4100(DE3) harboring pDP3615 | Herein |

TABLE 2-continued

*E. coli* strains and plasmids used in this work

| Strain or Plasmid | Description | Reference or source |
|---|---|---|
| DP-E3616 | MC4100(DE3) harboring pDP3616 | Herein |
| DP-E3617 | MC4100(DE3) harboring pDP3615 and pDP3616 | Herein |
| DP-B3618 | JM109(DE3) harboring pDH70 | Herein |
| DP-E3619 | JM109(DE3) harboring pDP3615 and pDH70 | Herein |

$Ap^r$, ampicillin resistant; $Tc^r$, tetracycline resistant; $Kan^r$, kanamycin resistant; $Cm^r$, chloramphenicol resistant; $St^r$, streptomycin resistant Plasmid pDP3615 was generated by PCR amplification of the hly gene encoding LLO lacking its secretion signal sequence (22). DNA sequences encoding mature LLO were first PCR amplified and cloned into pET29b (Novagen, Inc., Madison, Wis.) using oligonucleotide primer 5'-GGAATTCCATATGAAGGATGCATCTGCATTCAAT-3' (SEQ ID NO:1) generating a NdeI restriction site at the 5' end of the gene fragment and primer 5'-CGGGATCCTTATTATTCGATTGGATTATCTACT-3' (SEQ ID NO:2) generating a BamHI restriction site at the 3' end of the gene fragment. Following ligation into the pET29b vector, the DNA sequences encoding mature LLO along with the upstream translation initiation site found in pET29b were amplified using primer 5'-CGCGATATCCTCTAGAAATAATTTTG-3' (SEQ ID NO:3) generating an EcoRI restriction site at the 5' end of the gene fragment and the same primer used previously to generate a BamHI restriction site at the 3' end of the gene fragment. The amplified fragment was ligated into pACYC184 (23) placing transcription of the mature hly gene under control of the tet gene promoter. Plasmid pDP3616 was generated by subdloning a NcoI-HindIII fragment containing DNA sequences encoding truncated OVA from plasmid pTrcHisC/OVA. The DNA fragment was ligated into the over-expression vector pET28a (Novagen, Inc., Madison, Wis.). Plasmid pDH70 was generated by PCR amplification of the promoterless lacZ gene in plasmid pTL61T (24) using oligonucleotide primers 5'-AGGCGTCGACGGTTAATACGACCGGGATCGAG-3' (SEQ ID NO:4) and 5'-AGGCGTCGACAGGCC TTACGCGAAATACGGGCAGACATGG-3' (SEQ ID NO:5) generating SalI restriction sites at both the 5' and 3' ends of the fragment. The amplified fragment was ligated into pBluescript SK- (Stratagene, Inc., La Jolla, Calif.) placing transcription of the lacZ gene under control of a phage T7 promoter. Plasmid DNA was transferred to *E. coli* strains by transformation, using standard methods (25). *E. coli* strains were grown in Luria-Bertani (LB) medium. The strains were stored at −70° C. in LB medium plus 40% glycerol. Antibiotics were used at the following concentrations: ampicillin, 100 μg/ml; chloramphenicol, 40 μg/ml; and kanamycin, 30 μg/ml.

Expression of Target Proteins. *E. coli* strains were inoculated from a LB agar plate into 2 mils of LB medium and grown overnight to stationary phase at 37° C. with aeration. Cultures were diluted 1:100 in 10 mls of LB medium in 250 ml flasks and grown 2 hours with aeration at 30° C. Target protein expression was induced by the addition of isopropyl-β-D-thiogalactopyranoside (IPTG) to 1 mM and growth continued until cultures reached an $OD_{600}$ of 0.5. Equivalent numbers of bacteria were centrifuged (14,000×g) for 1 minute and washed once with phosphate buffered saline (PBS). Washed samples were suspended in Final Sample Buffer (0.0625M Tris pH 6.8, 2% SDS, 10% glycerol, 0.01% bromophenol blue) boiled for 5 minutes and total cellular protein analyzed by polyacrylamide gel electrophoresis followed by staining with Coomassie Brilliant Blue.

Determination of Hemolytic Activity. Following bacterial growth and induction of target proteins, 1 ml aliquots of bacteria were centrifuged (14,000×g) for 1 minute and washed once with PBS. Samples were resuspended in 1 ml of PBS and lysed by sonication. Soluble extract fractions were obtained by centrifuging lysed samples for 10 minutes (14, 000×g) at 4° C. and saving the supernatant. Hemolytic activity in the soluble fractions was determined as previously described (26) and is expressed as the reciprocal of the dilution of extracts required to lyse 50% of sheep erythrocytes.

Cell Culture. Cell lines were maintained in RPMI 1640 medium or DMEM supplemented with 10% fetal bovine serum (Hyclone Laboratories, Inc., Logan, Utah), 2 mM glutamine, 1 mM pyruvate, 50 μM 2-mercaptoethanol, penicillin (200 units/ml), and streptomycin (200 μg/ml) at 37° C. in a 5% $CO_2$/air atmosphere. The IC-21 and Raw 309 Cr.1 mouse macrophage cell lines were obtained from the American Type Culture Collection (ATCC, Rockford, Md.). The B3Z T-cell hybrid is a LacZ-inducible $CD8^+$ T-cell hybridoma specific for OVA residues 257–264, SIINFEKL (SL8) (SEQ ID NO:6), presented on the murine $K^b$ MHC class I molecule (27, 28).

Delivery of Protein to the Cytosol of Macrophages. IC-21 cells were seeded onto 18 mm glass coverstips in 35 mm dishes in RPMI medium without antibiotics. One hour prior to addition of bacteria, dishes were placed at 4° C. Medium was removed from the dishes and *E. coli* were added in cold RPMI medium without antibiotics to obtain an infection ratio of one bacterium/macrophage. Samples were incubated at 4° C. for one hour to allow association of bacteria and macrophages. Samples were washed five times with 3 mls of cold PBS and 37° C. RPMI medium added. Samples were incubated at 37° C. in a 5% $CO_2$/air atmosphere for up to one hour. At varying intervals during incubation of macrophages and *E. coli*, coverslips were removed and fixed for subsequent detection of protein.

Detection of Target Protein in Macrophages. Following delivery of β-gal to macrophages, coverslips were fixed in cold 2% formaldehyde/0.2% glutaraldehyde for 5 minutes at 4° C. β-gal activity was detected by staining with 5-bromo-4-chloro-3-indolyl β-galactopyranoside (X-gal, Sigma Immunochemicals, St. Louis, Mo.) as previously described (27). For detection of OVA, coverstips were fixed in 3.2% electron microscopy grade paraformaldehyde (Electron Microscopy Sciences, Ft. Washington, Pa.) overnight at 4° C. in aluminum foil wrapped containers. OVA was detected by immunofluorescence as previously described (29) with the exception that polyclonal rabbit anti-OVA antibody (Calbiochem, San Diego, Calif.) and LRSC-conjugated donkey anti-rabbit IgG antibody (Jackson ImmunoResearch, West Grove, Pa.) were used for detection.

Antigen Presentation Assays. Presentation of SL8/$K^b$ complex to B3Z cells was determined as previously described (30). Briefly, *E. coli* were added to $1\times10^5$ antigen presenting cells (APCs) in each well of a 96-well microtiter plate. Following one hour of incubation at 37° C. in a 5% $CO_2$/air atmosphere, extracellular bacteria were removed by washing three times with PBS and $1\times10^5$ B3Z T cells were added to each well in medium containing 100 $\mu$g/ml gentamicin. Following 15 hours of incubation at 37° C. in a 5% $CO_2$/air atmosphere, cultures were washed once with PBS and lysed by addition of 100 $\mu$l PBS buffer containing 100 $\mu$M 2-mercaptoethanol, 9 mM $MgCl_2$, 0.125% NP40, and 0.15 mM chlorophenolred-β-galactoside (CPRG, Calbiochem, San Diego, Calif.). After 4–6 hours at 37° C., 50 $\mu$l of stop buffer (300 mM glycine and 15 mM EDTA in water) was added and the absorbance at 570 nm of each well was determined using a 96-well plate reader. Where appropriate, APCs were fixed with 1% paraformaldehyde prior to the addition of B3Z cells as described (31). Synthetic SL8 peptide was obtained from Research Genetics, Inc. (Huntsville, Ala.) and was incubated with APCs and B3Z cells at a saturating concentration of 90 nM in RPMI medium.

Expression of Listeriolysin O and Target Proteins. To facilitate expression of mature cytoplasmic LLO in *E. coli*, the hly gene encoding LLO lacking its N-terminal signal sequence (22) was cloned into the plasmid vector pACYC184 to generate pDP3615 as described in Materials and Methods. Transcription of the truncated hly gene in pDP3615 is under the control of the constitutive tet gene promoter. Proteins to be delivered to the cytosol of macrophages were expressed from co-resident plasmids in *E. coli*. We chose chicken ovalbumin (OVA) as one of the representative proteins to deliver to the cytosol of macrophages. OVA is not toxic to *E. coli* and can be readily expressed to high levels (32). A plasmid encoding truncated (32 kD) OVA was transformed into *E. coli* along with pDP3615. In order to determine if a large protein with a measurable enzymatic activity could be delivered to the cytosol of macrophages, we expressed β-galactosidase (β-gal) along with LLO in *E. coli*. A plasmid containing the gene encoding β-gal, was transformed into *E. coli* along with plasmid pDP3615. Expression of both OVA and β-gal in these strains is under the control of IPTG-inducible phage T7 RNA polymerase. We next analyzed the hemolytic activity and protein expression profiles of these strains. Following IPTG induction, OVA and β-gal were expressed to approximately 20% of the total *E. coli* cellular protein as determined by SDS-PAGE. To verify expression of active LLO protein within *E. coli*, hemolytic activity contained in the soluble fraction of *E. coli* extracts was determined as described above. All of the strains expressing LLO contained approximately 500–600 hemolytic units of activity in the soluble extracts. No measurable hemolytic activity was found in the culture medium in which the *E. coli* were grown. These data indicate that functional LLO protein was contained within the *E. coli* cells and not secreted to the extracellular environment.

Delivery of Protein to the Cytosol of Macrophages. To examine the ability of *E. coli* expressing LLO to deliver a co-expressed target protein to the cytosol of macrophages, *E. coli* expressing LLO and OVA were added to macrophages to obtain an infection ratio of approximately one bacterium/macrophage. The presence of OVA either in phagosomes or in the cytosol was determined by immunofluorescence microscopy. When bacteria expressing OVA in the absence of LLO were added to macrophages, protein was contained within phagosomes and no OVA could be detected in the cytosol of macrophages within one hour following phagocytosis. In contrast, when bacteria expressing both LLO and OVA were added to macrophages, OVA protein could be detected throughout the entire cytosolic compartment within 30 minutes of bacterial uptake. Moreover, at least 50% of macrophages that had phagocytosed a single bacterium demonstrated release of OVA into the cytosol within 30 minutes following bacterial uptake. In some instances, OVA protein could be detected leaking from phagosomes into the cytosol as early as 10 minutes post-phagocytosis of bacteria.

Since release of OVA into the cytosol occurs subsequent to degradation of the *E. coli* within macrophage phagosomes, it was possible that proteins contained within the bacteria were also partially degraded or inactivated before release into the cytosol. To examine whether full-length β-gal could be delivered to the cytosol of macrophages and retain its biological activity, *E. coli* expressing LLO and β-gal were added to macrophages to obtain an infection ratio of approximately one bacterium/macrophage. β-gal activity in the cytosol was then determined by staining macrophages with X-gal. Our data indicate that β-gal activity could be detected throughout the cytosol within 30 minutes following bacterial uptake. Following phagocytosis of *E. coli* expressing β-gal in the absence of LLO, β-gal activity was detected sequestered within phagosomes. β-gal is a 116 kD protein that functions as a 465 kD tetramer (33). Whether β-gal is associated as a tetramer prior to release into the cytosol is unknown, but these data indicate that at a minimum a 116 kD protein can be delivered to the cytosol of macrophages using the *E. coli*/LLO delivery system and still retain its enzymatic activity.

Delivery of OVA to the MHC Class I Pathway for Antigen Presentation. Immunity to intracellular bacterial pathogens and viruses often requires the generation of cytotoxic T-lymphocytes (CTLs) that recognize and kill infected cells (13, 34, 35). Efficient processing and presentation of antigens to CTLs typically requires the endogenous synthesis of the antigen within the cytosol of the infected cell or introduction of the antigenic protein into the cytosol of an antigen presenting cell (APC) (36, 37). Once in the cytosol, proteases process the antigen to peptide epitopes which are subsequently presented on the surface of the APC in association with major histocompatibility (MHC) class I molecules for recognition by $CD8^+$ CTLs (37–39).

We wished to examine the ability of *E. coli* expressing LLO and an antigenic protein to deliver the antigen to the cytosol of macrophages for processing and presentation on MHC class I molecules. *E. coli* expressing LLO and OVA were added to macrophages and the processing and presentation of a peptide epitope derived from OVA was accessed using the B3Z T-cell hybrid. B3Z is a LacZ-inducible $CD8^+$ T-cell hybrid specific for OVA residues 257–264 (SIINFEKL, SEQ ID NO:6) presented on the murine $K^b$ MHC class I molecule (27, 28). The presentation of the SIINFEKL epitope (SL8) to B3Z cells results in the induction of β-gal synthesis by B3Z. The amount of β-gal produced can be measured by the hydrolysis of the chromogenic substrate CPRG and is an indication of the amount of SL8/$K^b$ complexes presented on the surface of APCs (27, 30). Bacteria were added to macrophages and phagocytosis allowed to proceed for one hour, followed by the removal of extracellular bacteria and addition of B3Z T-cells. As shown in FIG. 1, processing and presentation of SL8/$K^b$ to B3Z T-cells occurred when *E. coli* expressing both LLO and OVA were added to macrophages. In this figure, the indicated number of *E. coli* were added to $1\times10^5$ Raw 309 Cr.1 APCs in each well of a 96-well plate. Following one hour of incubation at 37° C. in a 5% $CO_2$/air atmosphere, extracellular bacteria were removed by washing with PBS and 1x$10^5$ B3Z T-cells were added to each well in medium containing 100 μg/ml gentamicin. Following 15 hours of incubation at 37° C. in a 5% $CO_2$/air atmosphere, presentation of SL8/$K^b$ to B3Z cells was assayed as described (27, 30) and indicated as an increase in the absorbance at 570 nm. *E. coli* strains added to APCs expressed LLO, DP-E3615 (○); OVA, DP-E3616 (●); or LLO and OVA, DP-E3617, (□). (■) indicates the level of activation obtained when APCs were incubated with 90 nM synthetic SL8 and B3Z cells. Data presented is from triplicate groups of wells from one of several repeated experiments with identical results. As shown, antigen presentation could be detected with as few as 1 bacterium added/10 macrophages. At a ratio of 10 bacteria added/macrophage, which resulted in the phagocytosis of one to two bacteria/macrophage, the level of presentation was equivalent to the maximal activity achieved by incubating macrophages with a saturating dose (90 nM) of synthetic SL8 peptide. No presentation of SL8/$K^b$ complex could be detected when *E. coli* expressing OVA in the absence of LLO were added to macrophages. Equivalent results were obtained when primary bone marrow and peritoneal derived macrophages were used in antigen presentation experiments. The decrease in absorbance seen when $10^7$ and $10^8$ LLO expressing bacteria were added was due to visible damage to the macrophages.

Processing and Presentation of SL8/$K^b$ Complex is Rapid. It has been previously demonstrated that OVA is efficiently processed and peptide/MHC complexes presented on the surface of APCs within two to four hours following delivery of OVA to the cytosol using alternative methods such as encapsulation in liposomes or scrape-loading (16, 20, 21). Data in FIG. 1 indicate that considerable processing and presentation of antigenic peptides can occur with as few as one bacterium added/macrophage. However, processing and presentation of antigen was allowed to occur for greater than 15 hours prior to measuring T-cell activation. It is possible that the time required for efficient processing of antigen has been altered by delivering protein to the cytosol using this method. We wished to examine the time necessary for antigen processing and presentation of peptide/MHC complexes when protein is delivered using the *E. coli*/LLO system.

Figure 2A:
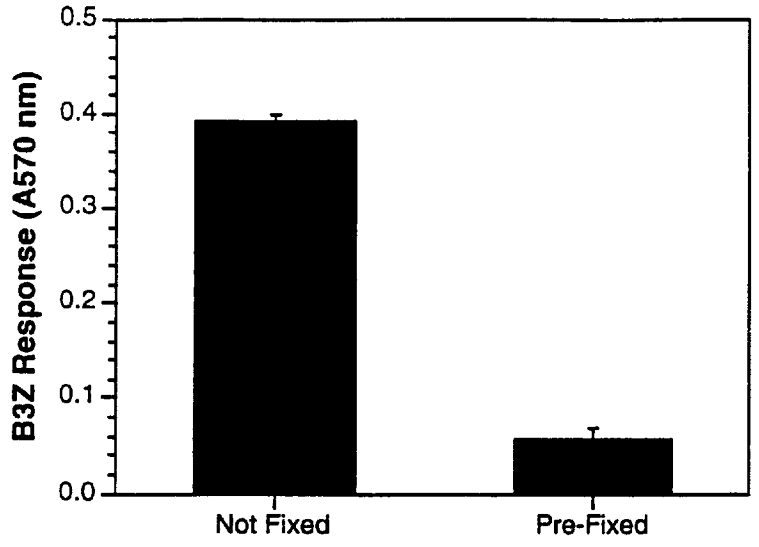
FIG. 2A and 2B. Time requirement for presentation of SL8/$K^b$ complex.

Paraformaldehyde fixation of macrophages prevents further phagocytosis of bacteria and has been shown to crosslink surface MHliC class I molecules to associated $\beta_2$-microglobulin (31). Thus, fixation stabilizes peptide/MHC complexes present on the cell surface and arrests any further processing and presentation of peptides. We examined the time required for antigen processing and presentation by fixing APCs with paraformaldehyde at varying intervals after addition of bacteria and measuring SL8/$K^b$ presentation to B3Z T-cells. First, the effect on antigen presentation of fixing macrophages prior to the addition of bacteria was addressed (FIG. 2A). In FIG. 2A, 1x$10^6$ *E. coli* strain DP-E3617 expressing LLO and OVA were added to 1x$10^5$ IC-21 macrophages in each well of a 96-well plate. Processing and presentation of SL8/$K^b$ was assayed as described in FIG. 1. Immediately prior to the addition of bacteria, APCs were either left untreated (Not Fixed) or fixed (Pre-Fixed) with 1% paraformaldehyde as described (31). Fixing APCs prior to the addition of bacteria completely abrogated the ability of macrophages to process and present SL8/$K^b$ complex to B3Z T-cells, as evident by an equivalent response as that seen when no bacteria were added to the macrophages (FIG. 1).

Figure 2B:
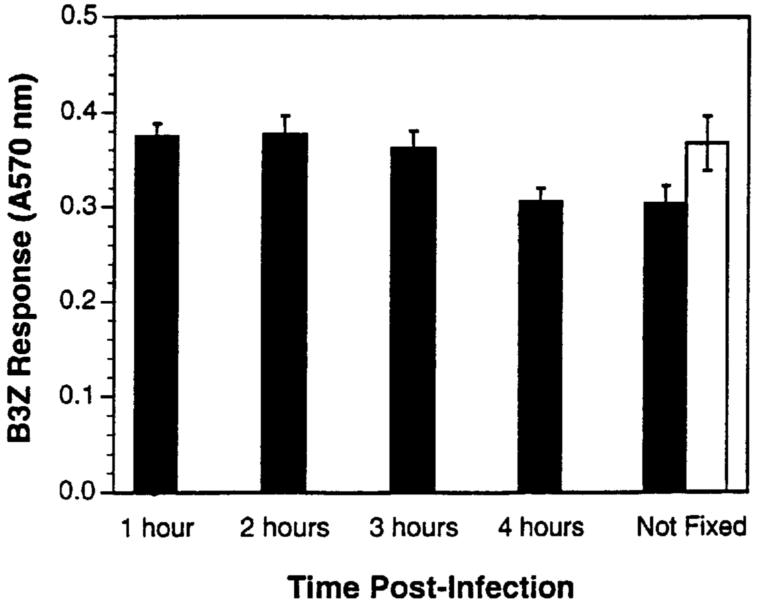

In FIG. 2B, the time requirement for processing and presentation of SL8/$K^b$ complex was addressed. Here, 1x$10^6$ *E. coli* strain DP-E3617 expressing LLO and OVA were added to 1x$10^5$ IC-21 APCs in each well of a 96-well plate. Following one hour of incubation at 37° C. in a 5% $CO_2$/air atmosphere, extracellular bacteria were removed by washing with PBS and APCs were either immediately fixed with 1% paraformaldehyde (1 hour) or incubated further in media containing 100 μg/ml gentamicin. At one hour intervals, APCs were fixed with 1% paraformaldehyde until all time points were completed. Following completion of the four hour time interval, APCs were washed with PBS and 1x$10^5$ B3Z T cells added to each well. Presentation of SL8/$K^b$ was assayed as described above. Labels indicate the time elapsed post addition of bacteria prior to fixation of APCs. Dark shaded bars indicate samples to which *E. coli* strain DP-E3617 were added. Light shaded bar indicates samples to which no bacteria but 90 nM synthetic SL8 was added with B3Z cells. The (Not Fixed) samples received no fixation prior to the addition of B3Z cells. Data presented is from triplicate groups of wells from one of three experiments with identical results.

Fixing APCs at one hour following the addition of *E. coli* expressing LLO and OVA resulted in sufficient antigen presentation to yield activation of B3Z cells to a level slightly higher than those seen in the absence of fixing (compare 1 hour fixed to Not Fixed). The increased level of SL8/$K^b$ presentation following fixation can be attributed to crosslinking of surface MHC class I molecules resulting in increased stability of peptide-MHC complexes (31). Consistent with previous studies of OVA delivery to APCs (16, 20, 21), the maximal presentation of SL8/$K^b$ complex occurred when processing of OVA was allowed to continue for two hours prior to fixation. This level of SL8/$K^b$ presentation was equivalent to that seen with the addition of 90 nM synthetic SL8 in the absence of fixation (FIG. 2B). Additional analysis indicated that fixing APCs later than two hours after addition of bacteria, resulted in a decreased level of SL8/$K^b$ presentation (FIG. 2B, 3 and 4 hour time points). This is consistent with dissociation of surface peptide/MHC complexes prior to crosslinking MHC class I molecules by fixation (31). These data indicate that no delay in the processing and presentation of SL8/$K^b$ complex occurred when OVA was delivered to the cytosol using the *E. coli*/LLO delivery system.

The results of this example demonstrate that *E. coli* expressing cytoplasmic LLO can be used to deliver a co-expressed protein to the cytosol of macrophages. The delivery of protein to macrophages was rapid and efficient with protein first appearing in the cytosol within ten minutes following bacterial uptake. Moreover, large enzymatically active proteins can be introduced into the cytosol using this method as demonstrated by the delivery of active β-gal. The mechanism of delivery may be as follows. Subsequent or concomitant to phagocytosis, the *E. coli* are killed and degraded within phagosomes causing the release of LLO and the target protein from the bacteria. LLO acts by forming large pores in the phagosomal membrane thus releasing the target protein into the cytosol. In any event, any protein that can be synthesized in *E. coli* can be delivered to the macrophage cytosol.

LLO is an essential determinant of pathogenesis whose role is to mediate release of *L. monocytogenes* from a phagosome. The biological properties of LLO make it well suited for use in our system. For example, LLO has an acidic pH optimum which facilitates its action in a phagosome (40, 41). However, it was unclear whether LLO released by degraded *E. coli* would retain its biological activity. The data presented here demonstrate that the amount of LLO expressed was sufficient to allow the rapid release of protein into the cytosol. Based on SDS-PAGE analysis of known quantities of purified LLO protein, we estimate approximately $1\times10^5$ molecules of LLO per *E. coli* cell. Using our disclosure, one can now determine how many molecules of LLO are actually needed to introduce a pore into a phagosome as described (42), where it was determined to take only approximately 50 molecules of streptolysin O, a homologous pore-forming cytolysin, to form a pore in red cell membranes. A second property of LLO is its relative lack of toxicity thought to be due to its proteolysis in the cytosol of host cells (43). Indeed, secretion by *L. monocytogenes* of a related pore-forming hemolysin, perfringolysin O, resulted in death of the infected cells (44). Other facultative intracellular pathogens, Shigellae, Salmonellae, and Yersiniae all induce macrophage apoptosis (14, 45), yet infection with *L. monocytogenes* is relatively benign (46). In the current study, even though we estimate each recombinant *E. coli* contained approximately $1\times10^5$ molecules of LLO, there was no evidence of toxicity until there were about 25 bacteria/macrophage.

There are a number of advantages and applications of the *E. coli*/LLO delivery system. Many methodologies for delivering protein to the cytosol of macrophages require the prior purification of the protein to be delivered. With the *E. coli*/LLO mediated delivery of protein, no protein purification is required, only expression of the target protein in *E. coli* is necessary. Furthermore, with many alternative methods, delivery is restricted to minute amounts of protein or a limited number of cells and the in vivo delivery of protein can not be achieved (2). Using the *E. coli*/LLO system, high levels of protein can be delivered to the cytosol of virtually all of the cells in culture. In addition, by expressing protein under the control of inducible promoters, the level of protein produced and ultimately delivered to the cytosol of macrophages can be controlled. This system can be used in vivo and by expressing invasive determinants from other bacterial species, the *E. coli* may be modified to enter cells other than macrophages. Furthermore, this system has applications for the delivery of pathogen-specific protein antigens or DNA.

The results of this example show that the *E. coli*/LLO system is particularly effective for the introduction of protein into the MHC class I pathway of antigen processing and presentation. We were able to detect antigen presentation with less than 1 bacterium/10 macrophages and observed a maximal response with as few as 1 to 2 bacteria/macrophage (FIG. 1). In addition, efficient processing and surface presentation of peptide/MHC complexes occurred rapidly, within 1–2 hours following addition of bacteria to macrophages (FIG. 2B). Delivery to the MHC class I pathway was enhanced greater than 4-logs compared to *E. coli* expressing OVA alone. This is a similar level of enhancement to that reported when OVA linked to beads was compared to soluble OVA for presentation with MHC class I molecules (47). It is clear from subsequent studies that the beads, like LLO, mediated disruption of the phagosome (21, 48). However, there was one report in which *E. coli* expressing OVA was able to deliver OVA to the MHC class I pathway (49). Here, delivery was proposed to occur by a non-conventional pathway involving extracellular peptide regurgitation of phagosomal processed antigens instead of transfer of protein from the phagosomal compartment to the cytosol. Nonetheless, our data clearly show undetectable levels of antigen presentation when *E. coli* lacking LLO yet expressing OVA to 20% of the total cellular protein were used to deliver OVA to macrophages. Perhaps the T-cells used in our studies were unable to detect presentation of SL8/$K^b$ complexes, when *E. coli* expressing OVA alone were used, because of inefficient processing and presentation via the non-conventional pathway. In the previous study, OVA was generated as fusions to Crl or LamB proteins. The efficiency of processing and presentation of epitopes from OVA has been shown to be dependent on the protein context surrounding the epitope (50, 51). Therefore, it is possible that the fusion proteins used in the previous study are processed more efficiently than the truncated OVA used in this report.

Recently, an *E. coli* expression cloning strategy for the identification of $CD4^+$ T cell-stimulating antigens has been reported (30). However, this method has not been successfully used to identify $CD8^+$ CTL-stimulating antigens since proteins expressed in *E. coli* do not gain efficient access to the AMC class I pathway for antigen presentation. The results of this study indicate that the *E. coli*/LLO delivery system provides an expression cloning strategy for the identification of pathogen-specific $CD8^+$ CTL-stimulating antigens. The identification of these pathogen-specific epitopes is an important step in the rational design of vaccine strategies against these infectious agents. These antigens are further characterized to determine the peptide epitopes recognized by CTLs, as well as the natural function the antigenic protein plays in the interaction of the pathogen and host cells.

The efficiency of antigen delivery provides for the E coli/LLO system to be used for the induction of CTLs in vivo. The efficient in vivo delivery of antigens to generate a protective immune response is a significant challenge in vaccine development. The use of bacterial vectors that have evolved to invade and replicate in mammalian cells such as Shigella (11, 12), Salmonella (8–10), and *Listeria monocytogenes* (52–55) are being explored as methods for the delivery of both protein antigens and DNA. Although these vehicles have had success in eliciting protective immune responses, the in vivo use of pathogenic bacteria has inherent risks. One strategy to overcome these obstacles has been to engineer attenuated *E. coli* that can invade and enter the cytosol of host cells for the delivery of macromolecules. *E. coli* deficient in the production of diaminopimelate (DAP), an essential cell wall component, undergo lysis during growth in the absence of DAP (56). DAP-minus *E. coli* carrying the 200 kb virulence plasmid pWR100 from *Shigella flexneri* have been engineered to deliver DNA to mammalian cells (11). These *E. coli* have the ability to invade cultured cells and enter the cytosol similar to *S. flexneri*, yet following brief replication, spontaneously lyse in the cytosol and allow for the delivery of DNA for subsequent expression in the host cell. However, the presence of the pWR100 virulence plasmid poses limitations on the suitability of this microbe for many applications. The rational design of safe delivery vectors is therefore of paramount importance when constructing new methodologies for in vivo delivery. Since the *E. coli*/LLO system does not contain any virulence associated determinants other than LLO, it is uniquely situated to safely deliver antigens to macrophages in vivo to generate a protective immune response.

Numerical References

1. Wong, T. K. & Neumann, E. (1982) *Biochem. Biophys. Res. Commun.* 107, 584–587.
2. Celis, J. E., ed. (1998) in *Cell Biology: a laboratory handbook*, 2nd. ed., Vol. 4. (Acad Press, San Diego, Calif.).

3. Rozengurt, E., et al. (1975) *Biochem. Biophys. Res. Commun.* 67, 1581–1588.
4. Grant, N. J., Aunis, D., & Bader, M. F. (1987) *Neuroscience* 23, 1143–1155.
5. Vile, R. G., Tuszynski, A., & Castleden, S. (1996)*Mol. Biotechnol.* 5, 139–158.
6. Adams, S. E., & Kingsman, A. J. (1995) *Pharm. Biotechnol.* 6, 769–786.
7. Dachs, G. U., et al. (1997) *Oncol Res.* 9, 313–325.
8. Darji, A., et al. (1997) *Cell* 91, 765–775.
9. Gentschev, I., et al. (1996) *Gene* 179, 133–140.
10. Hess, J., et al. (1996) *Proc. Natl. Acad. Sci. U.S.A.* 93, 1458–1463.
11. Courvalin, P., et al. (1995) *C. R. Acad. Sci. III* 318, 1207–1212.
12. Sizemore, D. R., Branstrom, A. A., & Sadoff, J. C. (1995) *Science* 270, 299–302.
13. Kaufmann, S. H. (1993) *Annu. Rev. Immunol.* 11, 129–163.
14. Finlay, B. B., & Cossart, P. (1997) *Science* 276, 718–725.
15. Portnoy, D. A., et al. (1992) *Infect. Immun.* 60, 1263–1267.
16. Lee, K. D., et al. (1996) *J. Biol. Chem.* 271, 7249–7252.
17. Darji, A., et al. (1997) *Eur. J. Immunol.* 27, 1353–1359.
18. Darji, A., et al. (1995) *Eur. J. Immunol.* 25, 2967–2971.
19. Mazzaccaro, R. J., et al. (1996) *Proc. Natl. Acad. Sci. U.S.A.* 93, 11786–11791.
20. Zhou, F., Watkins, S. C., & Huang, L. (1994) *Immunobiology* 190, 35–52.
21. Oh, Y. K., Harding, C. V., & Swanson, J. A. (1997) *Vaccine* 15, 511–518.
22. Darji, A., et al. (1995) *J. Biotechnol.* 43, 205–212.
23. Chang, A. C. Y., & Cohen, S. N. (1978) *J. Bacteriol.* 134, 1141–1156.
24. Linn, T., & St. Pierre, R. (1990) *J. Bacteriol.* 172, 1077–1084.
25. Sambrook, J., et al. (1989) in *Molecular cloning: a laboratory manual*, eds. Ford, N., Nolan, C. & Ferguson, M. (Cold Spring Harbor Laboratory Press, Cold Spring Harbor, N.Y.)
26. Portnoy, D. A., Jacks, P. S., & Hinrichs, D. J. (1988) *J. Exp. Med.* 167, 1459–1471.
27. Sanderson, S., & Shastri, N. (1994) *Int. Immunol.* 6, 369–376.
28. Karttunen, J., et al. (1992) *Proc. Natl. Acad. Sci. U.S.A.* 89, 6020–6024.
29. Marquis, H., Goldfine, H., & Portnoy, D. A. (1997) *J. Cell Biol.* 137, 1381–1392.
30. Sanderson, S., Campbell, D. J., & Shastri, N. (1995) *J. Exp. Med.* 182, 1751–1757.
31. Rock, K. L., etal. (1992) *J. Immunol.* 148, 1451–1457.
32. Takahashi, N., Orita, T., & Hirose, M. (1995) *Gene* 161, 211–216.
33. Jacobson, R. H., et al. (1994) *Nature* 369, 761–766.
34. Kagi, D., et al. (1996) *Annu. Rev. Immunol.* 14, 207–232.
35. Singh, N., Agrawal, S., & Rastogi, A. K. (1997) *Emerg. Infect. Dis.* 3, 41–49.
36. Harding, C. V. (1996) *J. Clin. Immunol.* 16, 90–96.
37. York, I. A., & Rock, K. L. (1996) *Annu. Rev. Immunol.* 14, 369–396.
38. Craiu, A., et al. (1997) *Proc. Natl. Acad. Sci. U.S.A.* 94, 10850–10855.
39. Rock, K. L., et al. (1994) *Cell* 78, 761–771.
40. Geoffroy, C., et al. (1987) *Infect. Immun.* 55, 1641–1646.
41. Beauregard, K. E., et al. (1997) *J. Exp. Med.* 186, 1159–1163.
42. Sekiya, K., et al. (1993) *J. Bacteriol.* 175, 5953–5961.
43. Villanueva, M. S., Sijts, A. J., & Pamer, E. G. (1995) *J. Immunol.* 155, 5227–5233.
44. Jones, S., & Portnoy, D. A. (1994) *Infect. Immun.* 62, 5608–5613.
45. Ruckdeschel, K., et al. (1997) *Infect. Immun.* 65, 4813–4821.
46. Barsig, J., & Kaufmnann, S. H. (1997) *Infect. Immun.* 65, 4075–4081.
47. Kovacsovics-Bankowski, M., et al. (1993) *Proc. Natl. Acad. Sci. USA* 90, 4942–4946.
48. Kovacsovics-Bankowski, M., & Rock, K. L. (1995) *Science* 267, 243–246.
49. Pfeifer, J. D., et al. (1993) *Nature* 361, 359–362.
50. Svensson, M., et al. (1997) *Behring Inst. Mitt.* 98, 197–211.
51. Shastri, N., Serwold, T., & Gonzalez, F. (1995) *J. Immunol.* 155, 4339–4346.
52. Frankel, F. R., et al. (1995) *J. Immunol.* 155, 4775–4782.
53. Ikonornidis, G., et al. (1997) *Vaccine* 15, 433–440.
54. Shen, H., et al. (1995) *Proc. Natl. Acad. Sci. U.S.A.* 92, 3987–3991.
55. Pan, Z. K., et al. (1995) *Nat. Med.* 1, 471–477.
56. Patte, J. C. (1996) in *Biosynthesis of Threonine and Lysine*, eds. Neidhardt, F. C., et al. (ASM Press, Washington, D.C.), pp. 528–541.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A nonvirulent bacterium comprising a first gene encoding a nonseceted foreign functional cytolysin operably linked to a heterologous promoter which expresses the cystolysin in the bacterium, and a second gene encoding a different foreign agent.

2. The bacterium of claim 1, wherein the cytolysin is absent a functional signal sequence.

3. The bacterium of claim 1, wherein the cytolysin is listeriolysin.

4. The bacterium of claim 1, wherein the bacterium further comprises a third gene encoding an invasin and a fourth gene encoding an autolysin.

5. The bacterium of claim 1, wherein the bacterium is a laboratory strain of *E. coli.*

6. The bacterium of claim 1, wherein the foreign agent is therapeutic to a eukaryote.

7. An isolated eukaryotic cell comprising the nonvirulent bacterium of claim 1 further comprising the foreign cytolysin.

8. The cell of claim 7, wherein the cell is phagocytic, pathogenic or diseased cell.

9. A method for introducing a foreign agent into a eukaryotic cell comprising the step of contacting the cell with the bacterium of claim 1 under conditions whereby the agent enters the cell.

10. The method of claim 9, wherein the bacterium is endocytosed into a vacuole of the cell, the bacterium undergoes lysis and the cytolysin mediates transfer of the agent from the vacuole to the cytosol of the cell.

11. The method of claim 9, wherein the bacterium is dead or non-viable.

12. The method of claim 9, wherein the bacterium comprises the cytolysin.

13. The method of claim 9, wherein the agent is synthesized by the bacterium.

14. The method of claim 9, wherein the bacterium is engineered to deliver libraries of agents for screening.

15. The method of claim 9, wherein the bacterium is engineered to deliver to antigen-presenting cells antigenic polypeptides which are presented in association with MHC proteins.

16. The method of claim 9, wherein the bacterium is nonreplicative and nonintegrative into the host cell genome.

17. The method of claim 9, wherein the bacterium is a dead or nonviable laboratory strain of *E. coli.*

18. The method of claim 9, wherein the bacterium is a laboratory strain of *E. coli* and the bacterium comprises the cytolysin.

19. The method of claim 9, wherein the bacterium is a dead or nonviable laboratory strain of *E. coli* and the bacterium comprises the cytolysin.

20. The method of claim 9, wherein the bacterium is a dead or nonviable laboratory strain of *E. coli* and the bacterium comprises the cytolysin and the cytolysin is listeriolysin.

21. The method of claim 9, wherein the bacterium is a laboratory strain of *E. coli* engineered to deliver to antigen-presenting cells antigenic polypeptides which are presented in association with MHC proteins.

22. The method of claim 9, wherein there is no growth or metabolism of the bacterium in the eukaryotic cell.

23. The bacterium of claim 1, wherein the bacterium is dead or non-viable.

24. The bacterium of claim 1, wherein the bacterium comprises the cytolysin.

25. The bacterium of claim 1, wherein the agent is synthesized by the bacterium.

26. The bacterium of claim 1, wherein the bacterium is engineered to deliver libraries of agents for screening.

27. The bacterium of claim 1, wherein the bacterium is engineered to deliver to antigen-presenting cells antigenic polypeptides which are presented in association with MHC proteins.

28. The bacterium of claim 1, wherein the bacterium is nonreplicative and nonintegrative into the host cell genome.

29. The bacterium of claim 1, wherein the bacterium is a dead or nonviable laboratory strain of *E. coli.*

30. The bacterium of claim 1, wherein the bacterium is a laboratory strain of *E. coli* and the bacterium comprises the cytolysin.

31. The bacterium of claim 1, wherein the bacterium is a dead or nonviable laboratory strain of *E. coli* and the bacterium comprises the cytolysin.

32. The bacterium of claim 1, wherein the bacterium is a dead or nonviable laboratory strain of *E. coli* and the bacterium comprises the cytolysin and the cytolysin is listeriolysin.

33. The bacterium of claim 1, wherein the bacterium is a laboratory strain of *E. coli* engineered to deliver to antigen-presenting cells antigenic polypeptides which are presented in association with MEC proteins.

* * * * *

US006004815C1

(12) EX PARTE REEXAMINATION CERTIFICATE (6475th)

United States Patent

Portnoy et al.

(10) Number: US 6,004,815 C1

(45) Certificate Issued: Oct. 14, 2008

(54) BACTERIA EXPRESSING NONSECRETED CYTOLYSIN AS INTRACELLULAR MICROBIAL DELIVERY VEHICLES TO EUKARYOTIC CELLS

(75) Inventors: Daniel A. Portnoy, Berkeley, CA (US); Darren E. Higgins, Berkeley, CA (US)

(73) Assignee: The National Institutes of Health, Bethesda, MD (US)

Reexamination Request:
No. 90/008,860, Nov. 7, 2007

Reexamination Certificate for:

| | |
|---|---|
| Patent No.: | **6,004,815** |
| Issued: | **Dec. 21, 1999** |
| Appl. No.: | **09/133,914** |
| Filed: | **Aug. 13, 1998** |

(51) Int. Cl.

| | |
|---|---|
| ***A61K 39/00*** | (2006.01) |
| ***C12N 15/63*** | (2006.01) |
| ***C12N 15/87*** | (2006.01) |

(52) U.S. Cl. ..................... 435/454; 424/200.1; 435/325; 435/373; 435/252.33; 435/252.3

(58) Field of Classification Search ........................ None
See application file for complete search history.

(56) References Cited

U.S. PATENT DOCUMENTS 5,824,538 A 10/1998 Branstrom et al.

OTHER PUBLICATIONS

Galan (J.Bacteriol. 1992, Jul.; 174(13): 4338–4339).*

Gentschev I, et al. "Development of antigen–delivery systems, based on the *Escherichia coli*hemolysin pathway" Gene 179 (1996) 133–140.

Bielecki J., et al. "Bacillus subtillis expressing a haemolysin gene from *Listeria monocytogenes* can grow in mammalian cells" Nature: (1990) 345: 6271, 175–176.

Hess J., et al "*Mycobacterium bovis* bacilli Calmette–Guerin strains secreting listeriolysin of *Listeria monocytogenes*" Proc. Natl. Acad. Sci. vol. 95, pp. 5299–5304, 1998.

Schmidt H., et al. "Molecular Analysis of the Plasmid–Encoded Hemolysin of *Escherichi coli*O157:H7 Strain EDL 933" Infection and Immunity, (1995) vol. 63, No. 3, pp. 1055–1061.

Dietrich G et al., "Delivery of antigen–encoding plasmid DNA into the cytosol of macrophages by attenuated suicide *Listeria monocytogenes*" Nature Biotechnology vol. 15 (1998) pp. 181–185.

* cited by examiner

*Primary Examiner*—Padmashri Ponnaluri

(57) ABSTRACT

The invention provides methods and compositions relating to intracellular delivering of agents to eukaryotic cells. The compositons include microbial delivery vehicles such as nonvirulent bacteria comprising a first gene encoding a non-secreted foreign cytolysin operably linked to a heterologous promoter and a second gene encoding a different foreign agent. The foreign agent may be a nucleic acid or protein, and is frequently bioactive in and therapeutic to the target eukaryote. In addition, the invention provides eukaryotic cells comprising the subject nonvirulent bacteria and nonhuman eukaryotic host organisms comprising such cells.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 2 is cancelled.

Claims 1, 33 are determined to be patentable as amended.

Claims 3–32, dependent on an amended claim, are determined to be patentable.

1. A nonvirulent bacterium comprising a first gene encoding a [nonseceted] *nonsecreted* foreign functional cytolysin operably linked to a heterologous promoter which expresses the cystolysin in the bacterium, and a second gene encoding a different foreign agent*, wherein the cytolysin is absent a functional signal sequence*.

33. The bacterium of claim 1, wherein the bacterium is a laboratory strain of E. coli engineered to deliver to antigen-presenting cells antigenic polypeptides which are presented in association with [MEC] *MHC* proteins.

* * * * *